United States Patent
Chen et al.

(10) Patent No.: US 7,499,522 B2
(45) Date of Patent: Mar. 3, 2009

(54) CARGO SECURITY INSPECTION SYSTEM AND METHOD

(75) Inventors: Zhiqiang Chen, Beijing (CN); Li Zhang, Beijing (CN); Kejun Kang, Beijing (CN); Haifeng Hu, Beijing (CN); Yuanjing Li, Beijing (CN); Yinong Liu, Beijing (CN); Hewei Gao, Beijing (CN); Ziran Zhao, Beijing (CN); Yuxiang Xing, Beijing (CN); Yongshun Xiao, Beijing (CN); Jianmin Li, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 11/801,272

(22) Filed: May 8, 2007

(65) Prior Publication Data

US 2008/0075226 A1    Mar. 27, 2008

(30) Foreign Application Priority Data

May 8, 2006    (CN)    ......................... 2006 1 0076573

(51) Int. Cl.
G01N 23/04    (2006.01)

(52) U.S. Cl. ............................... 378/57; 378/9; 378/10; 378/20

(58) Field of Classification Search ..................... 378/4, 378/9, 10, 20, 21, 57, 58, 62, 208; 250/548, 250/358.1, 359.1, 360.1
See application file for complete search history.

(56) References Cited

U.S. PATENT DOCUMENTS 5,864,600 A * 1/1999 Gray et al. ..................... 378/57

* cited by examiner

Primary Examiner—Jurie Yun
(74) Attorney, Agent, or Firm—Kenyon & Kenyon LLP

(57) ABSTRACT

A cargo security inspection system inspecting an object moving through the system, including: a mechanical conveyance unit carrying, conveying, and defining a travel path of the object in the system; a radiation-generating unit generating ray beams for transmitting through the object; and a data collecting unit collecting transmission data about the rays having already transmitted through the object and processing the transmission data; wherein the travel path includes at least two linear sub-paths at an angle relative to each other; the data collecting unit includes at least two detector arrays receiving ray beams, each detector array corresponding to one linear sub-path, a receiving plane of each of the detector arrays disposed parallel to its corresponding linear sub-path; and in use, the radiation-generating and data collecting units remain stationary, and the object travels along its travel path and only translates on the at least two linear sub-paths without any rotation.

22 Claims, 6 Drawing Sheets

CARGO SECURITY INSPECTION SYSTEM AND METHOD

CROSS-REFERENCE TO RELATED APPLICATION

This application claims priority under 35 U.S.C. § 119 to Chinese Patent Application No. 200610076573.8, filed May 8, 2006, the entire contents of which is hereby incorporated by reference.

FIELD OF THE INVENTION

The present invention relates to radiation imaging, in particular, to a cargo security inspection system.

BACKGROUND INFORMATION

Security inspection is of great importance in fields such as anti-terrorism and fighting against trafficking in drugs and smuggling. After 9/11 terrorist attacks of the United States, countries in the whole world more and more stress security inspection, and particularly take a series of security inspection measures to rigidly inspect passengers' luggage and articles and cargo containers at public sites such as airports, bus stations, the Customs House and docks.

At present, the mainstream imaging technology extensively used for security inspection systems is radiation imaging technology. According to exponential decay theory of radiation rays (photons), the radiation imaging technology works as follows: a radiation source is used to irradiate an inspected object from one side of said inspected object; the rays, after transmitting through the inspected object, are received by a ray collecting means; the ray collecting means converts the received rays into transmission data in digital form; the transmission data are combined into projection data which are then output to a computer for imaging; and the computer processes the collected data, synthesizes or reconstructs an image and displays it. A security inspection system using radiation imaging technology can carry out tomographic imaging or radiographic imaging. Tomographic imaging shows a tomographic image of the inspected object and combines multiple layers of tomographic images into a 3-dimensional image; radiographic imaging shows a 2-dimensional perspective image of the inspected image.

Since tomographic imaging requires the ray collecting means to receive all-round irradiation to the inspected object to obtain transmission projection data of the ray beams, a tomographic imaging security inspection system generally needs a computed tomography (CT) apparatus wherein at least one of the inspected object and the radiation source needs to rotate. In practical application, a security inspection system generally is required to inspect in an on-line real-time manner with a fast imaging speed. For example, articles carried by civil aviation are inspected at the Customs House at a rate of 0.5 m per second, so it is hard for even a spiral CT apparatus with a large screw pitch to meet the foregoing requirement. Besides, for large-size objects such as containers at the Customs House, it is very difficult for a container or a radiation source to rotate. Additionally, a CT apparatus is costly. Because of the above factors, security inspection systems using a CT apparatus for 3-dimensional imaging are not extensively applied.

In contrast with the tomographic imaging security inspection systems, a radiographic imaging security inspection system is widely used at public sites such as airports, bus stations, the Customs House and docks. However, the radiographic imaging security inspection system cannot avoid the overlapping effect of the objects in the direction of rays, and cannot solve the overlapping deficiency of the objects in the direction of rays so that the inspection capacity of the radiographic imaging security inspection system is seriously insufficient.

SUMMARY OF THE INVENTION

In view of the above, a main object of the present invention is to provide a cargo security inspection system to meet the requirement of quick imaging of security inspection systems, and to solve the problems of difficult rotation of large-size objects and the overlapping deficiency of the object in the direction of rays according to a radiographic imaging security inspection system.

To achieve the above object, the technical solution of the present invention is fulfilled as follows.

An embodiment of the present invention provides a cargo security inspection system for inspecting an inspected object moving through said system, the system comprising: a mechanical conveyance unit for carrying and conveying said inspected object and defining a travel path of the inspected object in said system; a radiation-generating unit for generating ray beams for transmitting through the inspected object; and a data collecting unit for collecting transmission data about the rays having already transmitted through the inspected object and processing said transmission data; wherein said travel path of said inspected object comprises at least two linear sub-paths that are arranged at an angle relative to each other; said data collecting unit comprises at least two detector arrays for receiving ray beams, each detector array corresponding to one linear sub-path, a receiving plane of each of said detector arrays being disposed parallel to the linear sub-path it corresponds to; and in use, the radiation-generating unit and the data collecting unit remain stationary, the inspected object travels along its travel path, and the inspected object only translates on said at least two linear sub-paths without any rotation.

Preferably, the system further comprises an imaging unit, wherein the data collecting unit combines the collected transmission data into projection data for outputting to the imaging unit, and the projection data is reconstructed as an image by the imaging unit.

Preferably, the system further comprises a display unit for displaying the image reconstructed by the imaging unit.

Preferably, the radiation-generating unit comprises one radiation source which is shared by all detector arrays or said radiation-generating unit comprises a plurality of radiation sources with each detector array corresponding to one radiation source.

Preferably, said mechanical conveyance unit comprises a conveyance means for supporting and conveying said inspected object and a control means for controlling the movement of said inspected object along the travel path.

Preferably, said mechanical conveyance unit is configured such that the inspected object only translates on each of said at least two linear sub-paths without any rotation.

Preferably, said mechanical conveyance unit is configured such that the inspected object only translates on each of said at least two linear sub-paths at a uniform speed without any rotation.

Preferably, the travel path of the inspected object further comprises a joint portion between adjacent linear sub-paths of said at least two linear sub-paths.

Preferably, said mechanical conveyance unit is configured such that the inspected object only translates at said joint portion without any rotation.

Preferably, said mechanical conveyance unit is configured such that the inspected object only translates on the whole travel path without any rotation.

Preferably, said mechanical conveyance unit is configured such that the inspected object only translates on the whole travel path at a uniform speed without any rotation.

Preferably, said radiation-generating unit and said data collecting unit are respectively provided on both sides of the travel path.

Preferably, said data collecting unit further comprises: a signal conversion circuit for converting the ray beam signals received by said detector arrays into the transmission data; a data processing circuit for combining the transmission data from the signal conversion circuit into the projection data; and a logic control circuit for controlling synchronous performance of the detector array receiving ray beam signals and the data processing circuit transmitting the projection data.

Preferably, said detector arrays are linear array detectors or planar array detectors.

Preferably, the detectors of said linear array detectors are arranged at an equal distance or equal angle from each other, and said planar array detectors are flat-panel detectors, cylindrical detectors or L-shaped detectors.

Preferably, said imaging unit reconstructs said projection data as a perspective image and/or a tomographic image.

Preferably, said imaging unit generates the tomographic image by a straight-line filtered backprojection algorithm.

Preferably, said detector arrays are planar array detectors, and said imaging unit further combines a plurality of tomographic images as a 3-dimensional image.

Preferably, said imaging unit combines said projection data to form a perspective image at a view angle or a plurality of perspective images at a plurality of view angles.

Preferably, said imaging unit treats the projection data by adopting one of or any combination of five processing manners: inconsistency of detectors, hardening, scatter correction, metal artifacts correction, and image processing and pattern recognition.

Preferably, said image processing and pattern recognition comprises one of or any combination of the following three processing modes: image enhancement, edge detection and hazardous article intelligent identification.

Preferably, the sum of the open angles of the receiving planes of the detector arrays relative to their respective radiation sources is substantially 180 degrees.

The security inspection system according to the present invention has the following advantageous effects as seen from the above technical solutions.

1. Since the present invention adopts linear sub-paths scanning in place of circular trajectory scanning or spiral trajectory scanning, the inspected object substantially performs a linear movement and the problem of centrifugal force occurring in a circular or spiral movement need not be considered. Thus, quick imaging can be achieved, and the imaging speed of the inspected object is substantially improved. The time for imaging the inspected object is reduced so as to greatly meet the requirement for the rate of articles being inspected in the Customs House, thereby further improving the rate of articles carried via aviation being inspected. The system has a promising application future and value in the market.

2. Since the present invention adopts linear sub-paths scanning in place of circular trajectory scanning or spiral trajectory scanning so that the inspected object substantially performs a linear movement, large-size objects needn't rotate, thereby solving the problem of difficult rotation of the large-size objects.

3. Since a tomographic image and a 3-dimensional image of the inspected object can be obtained according to the present invention, the present invention desirably solves the problem of overlapping of the object in the event of imaging via a conventional radiographic imaging security inspection system. Furthermore, conventional perspective images from a single or multiple perspectives can be obtained according to the present invention. The system of the present invention can carry out a preliminary inspection of the inspected object through the perspective image obtained first, and perform tomographic imaging when potential suspect areas are found so as to effect further inspection of said suspect areas.

4. Since the inspected object or the radiation source need not be rotated according to the present invention and the characteristic of linear transmission of the inspected object in the prior art security inspection system is utilized, the system of the present invention is very simple in mechanical design and low in costs.

DETAILED DESCRIPTION

The following embodiments are used to illustrate the present invention and not to limit the protection scope of the present invention.

The basic idea of the present invention is as follows. A travel path of an inspected object comprises at least two linear sub-paths that are arranged at an angle relative to each other, at least two detector arrays are respectively disposed corresponding to one of said linear sub-paths, and a receiving plane of each of said detector arrays is disposed parallel to the linear sub-path it corresponds to. In use, a radiation-generating unit and a data collecting unit remain stationary, the inspected object travels along its travel path, and the inspected object only translates on said at least two linear sub-paths without any rotation. In this manner, since the inspected object does not rotate on said at least two linear sub-paths, and the receiving planes of at least two detector arrays are arranged at an angle to each other, the inspected object is at different angles relative to said at least two detector arrays. In this way, the system according to the present invention can obtain transmission projection data of the inspected object from a larger angular range so as to effect computed tomography imaging of the inspected object and meanwhile effect conventional radiographic imaging of the inspected object at different angles. Particularly, when the sum of the open angles of the detector arrays relative to their respective radiation sources is approximately 180 degrees, the transmission projection data of the inspected object in all directions can be obtained so that an accurate tomography image is obtained.

Figure 1:
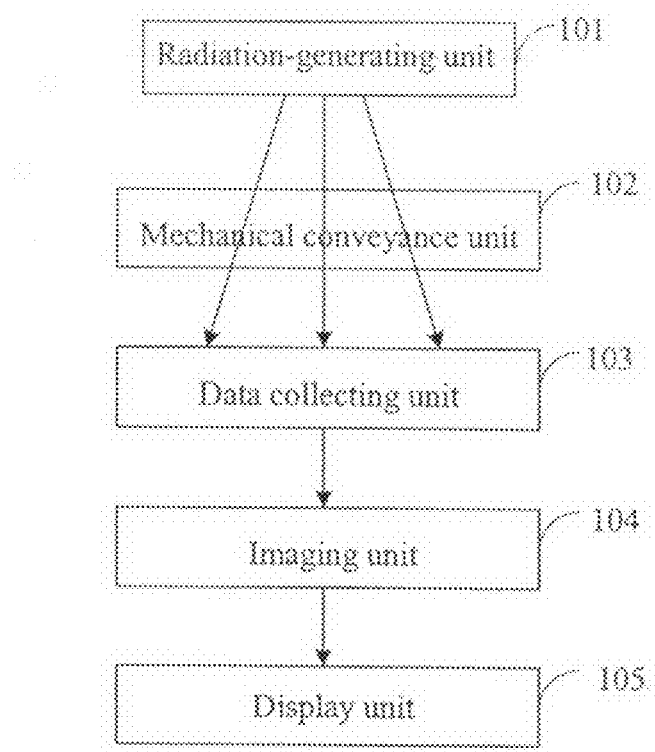
FIG. 1 is a block diagram showing the overall technical solution of the cargo security inspection system involving imaging on multiple linear sub-paths according to the present invention.

FIG. 1 is a block diagram showing the overall technical solution of the cargo security inspection system according to the present invention. As shown in FIG. 1, the system comprises a radiation-generating unit 101, a mechanical conveyance unit 102, a data collecting unit 103, an imaging unit 104 and a display unit 105.

The radiation-generating unit 101 is used to generate ray beams for transmitting through the inspected object, and the ray beams reach the data collecting unit 103 after transmitting through the inspected object. The radiation-generating unit 101 can be an X-ray tube, an accelerator radiation source or an isotope source. To generate ray beams with an opening angle of approximately 180 degrees, the radiation-generating unit 101 generally can use two or more radiation sources. Besides, the radiation-generating unit 101 can further comprise an auxiliary unit for alignment of and protection against rays and ensure that the opening angle of rays can cover the detector arrays in the data collecting unit.

The mechanical conveyance unit 102 is used to carry and convey said inspected object and defines the travel path of the inspected object in said system. The path defined by the mechanical conveyance unit 102 includes at least two linear sub-paths which are disposed at a certain angle relative to each other, which will be subsequently described in detail with reference to FIG. 3 and FIG. 7. The mechanical conveyance unit comprises conveyance means for supporting and conveying said inspected object and control means for controlling the movement of said inspected object along the travel path. The mechanical conveyance unit 102 conveys the inspected object in a direction parallel to a receiving plane of the data collecting unit 103, i.e., parallel to the receiving planes of the detector arrays in the data collecting unit 103. During movement of the inspected object along two or more linear sub-paths, in each of the linear sub-paths, the control means controls the conveyance means to convey said inspected object in a direction parallel to the receiving plane of the data collecting unit at a uniform speed such that the inspected object translates. Furthermore, when moving at a uniform speed at the joint between two adjacent linear sub-paths, the inspected object does not rotate. In general, the conveyance means can be a conveyance belt, a chain, rollers or the like, and the control means can be an electrical motor.

The data collecting unit 103 is used to receive the transmission data of the ray beams transmitting through the inspected object, and combine the received transmission data into projection data for output to the imaging unit 104. The data collecting unit 103 at least comprises a detector array, a signal conversion circuit, a data processing circuit and a logic control circuit. The detector array is used to receive the ray beam signals transmitting through the inspected object, the received ray beam signals are converted into transmission data via the signal conversion circuit, and the transmission data from the signal conversion circuit are combined into projection data by the data processing circuit. Furthermore, synchronous performance of the detector array receiving ray beam signals and the data processing circuit transmitting the projection data is controlled by the logic control circuit.

The data collecting unit 103 at least includes two detector arrays, wherein the number of the detector arrays is identical with that of the linear sub-paths. Furthermore, the receiving planes of the detector arrays are parallel to the corresponding linear sub-paths. In this manner, since the linear sub-paths are arranged at an angle relative to each other, the detector arrays are correspondingly disposed at a certain angle relative to each other. Furthermore, since the inspected object translates on the travel path thereof, it is at different angles respectively relative to said at least two detector arrays so that the ray beams can penetrate the inspected object at different angles to reach the respective detector arrays. To obtain transmission data in all directions as much as possible, the sum of the angles of the detector arrays receiving planes and their respective radiation sources is preferably approximately 180 degree. But, in some cases that requirement for accuracy is reduced and the sum can be less than 180 degrees.

Figure 2:
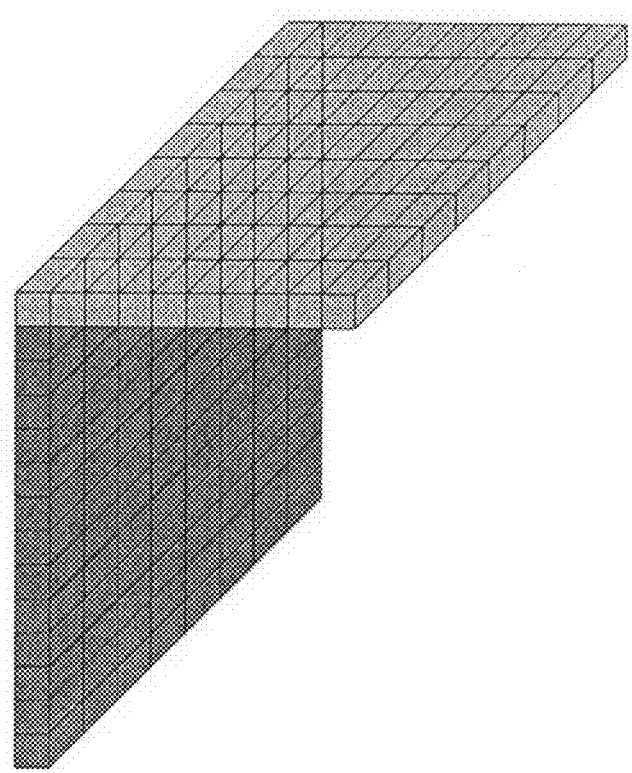
FIG. 2 is a schematic view of an L-shaped planar array detector.

The detector arrays can be linear array detectors or planar array detectors. The linear array detectors are arranged at an equal distance or equal angle from each other. The planar array detectors can be flat-panel detectors, cylindrical detectors or L-shaped detector, of which the L-shaped detector 200 is as shown in FIG. 2. Compared with flat-panel or cylindrical detectors, the L-shaped detector can substantially cut the number of detector when the L-shaped detector covers the object of the same height. The linear array detector or the planar array detector can be a solid detector, a gas detector or a semi-conductor detector. The detector array is generally disposed opposite a radiation source and the travel path of the inspected object is between the detector array and the radiation source.

Figure 3:
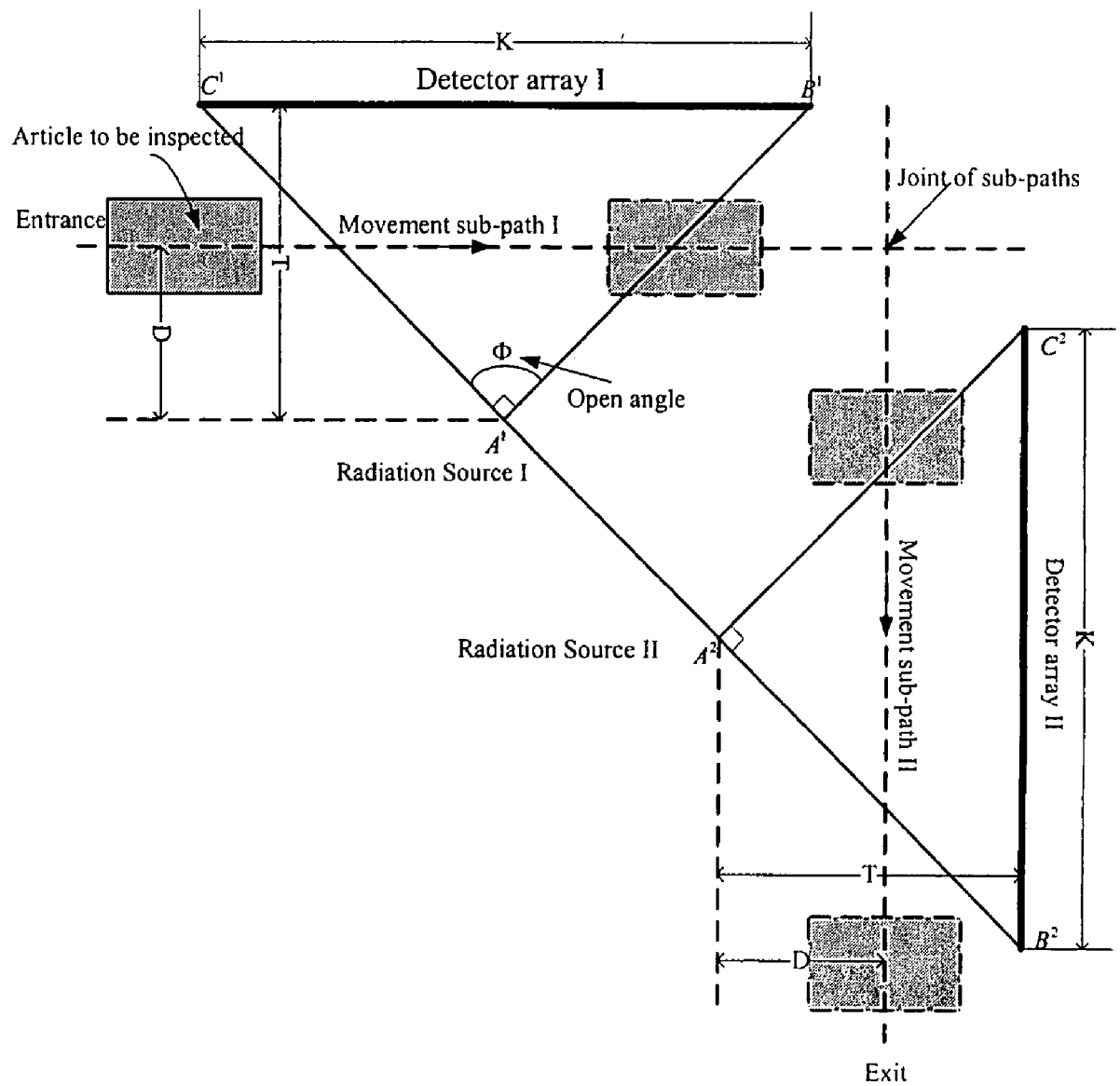
FIG. 3 is a plan view of the cargo security inspection system involving imaging at two linear sub-paths according to the first embodiment of the present invention.

In the cargo security inspection system involving scanning at two linear sub-paths, two detector arrays are needed, and the angle formed by the receiving planes of the two detector arrays is greater than 0 degree and less than 180 degrees. In general, the receiving planes of the two detector arrays form an angle of 90 degrees. The positional relations of said two detector arrays is shown in FIG. 3 which is a plan view of the cargo security inspection system involving imaging at two linear sub-paths according to the first embodiment of the present invention.

Figure 7:
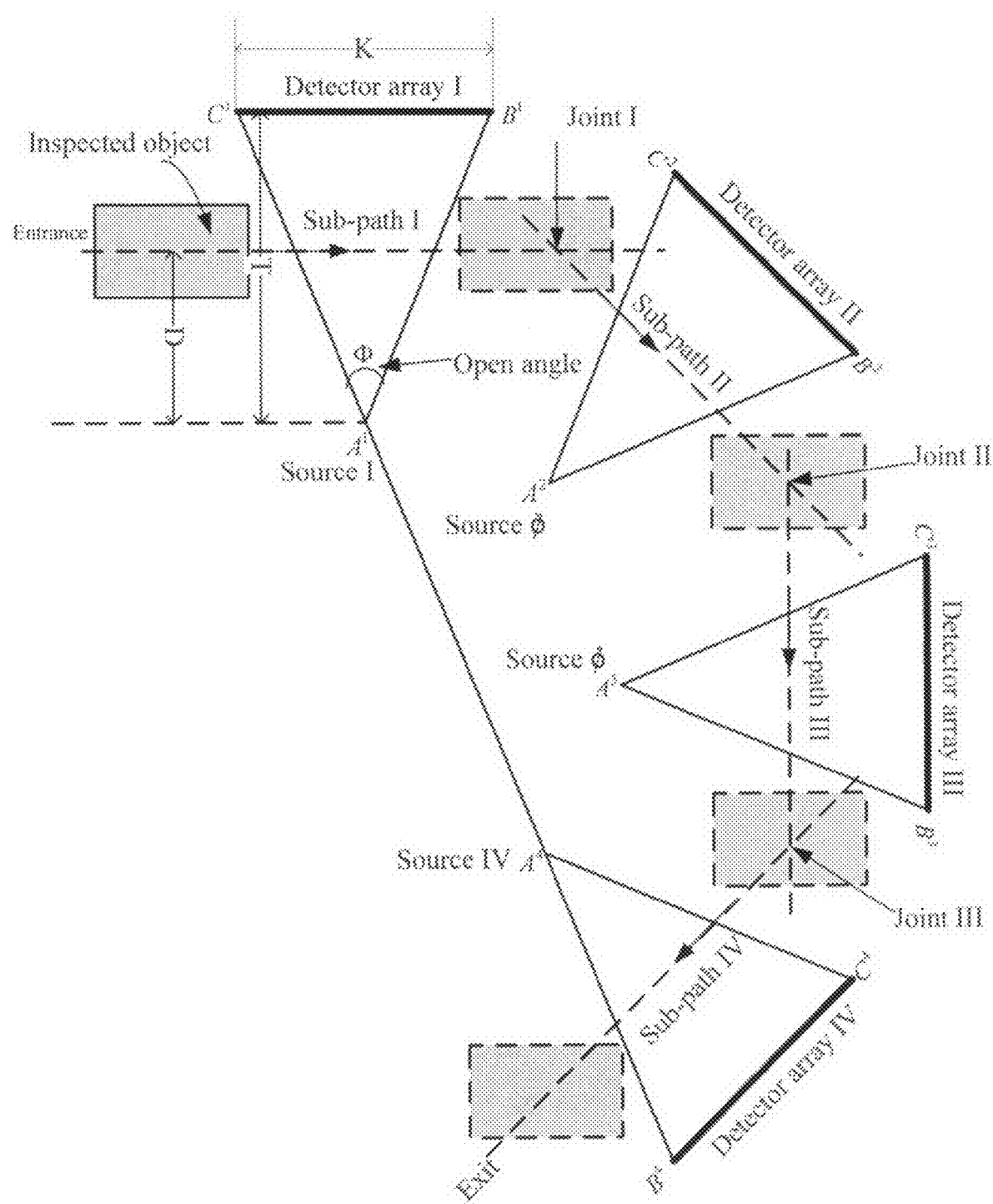
FIG. 7 is a plan view of the cargo security inspection system involving imaging at multiple linear sub-paths according to the second embodiment of the present invention.

In the cargo security inspection system involving scanning at multiple linear sub-paths, positional relations between the multiple detector arrays is illustrated in FIG. 7 which is a plan view of the cargo security inspection system involving imaging at multiple linear sub-paths according to the second embodiment of the present invention.

In the cargo security inspection system involving scanning at two or more linear sub-paths, if there are a plurality of detector arrays on a certain linear sub-path of the inspected object, the total length K of an individual section of detector array is related to the vertical distance T from the radiation source to the detector arrays: the greater the distance T is, the greater the total length K is, and $\Phi$, K and T satisfy the formula $K=2T \tan \Phi/2$. To obtain projection data of approximately 180 degrees, the ray beam opening angle $\theta$ and the number N of the linear sections satisfy the formula $\Phi=180/N$. The physical meanings of the parameter $\Phi$, K and T can be shown in FIG. 3 or FIG. 7.

When the detector array receives transmission data, since the time interval $\Delta t$ for receiving the transmission data is even, the inspected object moves at a uniform speed. Provided that the moving speed of the inspected object is v, the interval of space equivalent sampling of detector array receiving transmission data in the cargo security inspection system according to the present invention is Δd=vΔt. Besides, all the detector arrays conduct collecting data synchronously, and the data collecting unit combines the collected transmission data into projection data for outputting to the imaging unit 104. The projection data is reconstructed as tomographic image and/or perspective image by the imaging unit. At last, the image reconstructed by the imaging unit is displayed by the display unit.

The imaging unit 104 reconstructs the projection data received from the data collecting unit 103 as a tomographic image according to a straight-line filtered backprojection algorithm. By this algorithm, projection data obtained from the scanning of all the linear sub-paths are reconstructed, and all the reconstructions are incorporated together to form an ultimate tomographic image. This demonstrated as follows.

Provided that the detector arrays are in the data collecting unit 103, the data p(l, t, z) represents a projection value collected by the detector which is located at t in the $z^{th}$ layer when the object moves to the coordinate position l in X direction, wherein t, z are both values after the detector array corresponds to the centerline of the linear movement of the object. Furthermore, provided that D is the distance from the radiation source to the centerline of the linear movement, and $\pm t_m$ represents the maximum and minimum positions of the detector array in the X axis, an approximate estimate $\hat{f}(r, \phi, z)$ of the irradiated object $f(r, \phi, z)$ is as follows:

$$\hat{f}(r, \phi, z) = \int_{-t_m}^{t_m} \frac{1}{\sqrt{D'^2 + t^2}} Q\left(l', t, z\frac{D}{D + r\sin\phi}\right) dt$$

wherein, $$Q(l', t, z) = q(l, t, z) * h(l);$$

$$q(l, t, z) = p(l + t, t, z);$$

$$l' = r\cos\phi - \frac{tr\sin\phi}{D};$$

$$D' = \sqrt{D^2 + \left(z\frac{D}{D + r\sin\phi}\right)^2}; \text{ and}$$

h is a convolution kernel, with a theoretical value $$h(l) = \int_{-\infty}^{\infty} |\omega|e^{j2\pi\omega l}d\omega,$$

wherein an S-L filter function is generally used, and the discrete form of the function h is:

$$h(n) = \frac{-2}{\pi^2(4n^2 - 1)}, n = 0, \pm 1, \pm 2, \wedge$$

The straight-line filtered backprojection algorithm is characterized by effecting filter treatment of the received projection body data in the data collecting direction l, and integrating the received projection body data in the detector direction t to realize the back projection treatment. These characteristics are determined by linear scanning paths. Compared with the rebinning method of reassigning the collected data as parallel beams, the straight-line filtered backprojection algorithm can more sufficiently make use of each of the received valid projection data so as to maintain the resolution of the reconstructed image better and exhibits a sensitivity to truncation of data which is by far lower than the rebinning method.

If the imaging unit 104 reconstructs the projection data received from the data collecting unit as a tomographic image, the reconstruction process includes the following: the imaging unit effecting filter treatment of the projection data received from the data collecting unit in the data collecting direction by using the straight-line filtered backprojection algorithm, and integrating the filtered projection data in the detector direction to realize the back projection to generate a tomographic image. The imaging unit 104 can further combine the generated tomographic images as a 3-D image.

If the imaging unit 104 reconstructs the projection data received from the data collecting unit as a perspective image, the reconstruction process includes the following: the imaging unit combines the projection data received from the data collecting unit to form a perspective image from an individual perspective or a plurality of perspectives. In the foregoing combination step, the imaging unit can combine the data by using a certain column or more columns of data in the two or more detector arrays.

Furthermore, the process of the imaging unit 104 reconstructing the projection data received from the data collecting unit as an image further comprises the step of treating the transmission projection body data received from the data collecting unit by adopting one of or any combination of five processing manners: detector non-uniformity corrections, beam hardening correction, scatter correction, metal artifacts correction, and image processing and pattern recognition. Said image processing and pattern recognition comprises one of or any combination of the following three: image enhancement, edge detection and hazardous article intelligent identification.

The imaging unit 104 can be a computer apparatus, a computer work station or a computer cluster.

The display unit 105 is used to display the 3-D image or perspective image inputted by the imaging unit 104. Said display unit 105 can be a cathode ray tube (CRT) display or a liquid crystal display.

Embodiment 1

FIG. 3 is a plan view of the cargo security inspection system involving imaging at two linear sub-paths according to the first embodiment of the present invention.

In this embodiment, there are two X-ray sources, i.e., source I and source II serving as the radiation-generating unit 101. Said source I or said source II can be an X-ray tube, an accelerator source or an isotope source. Specific types of X-ray sources used depend on the dimensions of the inspected object and the practical application occasions. The X-ray source emits ray beams within an opening angle of 90 degrees and irradiates the inspected object in the horizontal direction.

The control means in the mechanical conveyance unit 102 controls the conveyance means to carry the inspected object to translate along the movement sub-path I and the movement sub-path II at a uniform speed, and furthermore, the inspected object does not rotate when moving at a uniform speed at the joint of the movement sub-path I and the movement sub-path II.

The data collecting unit 103 is two sets of planar array detectors respectively located opposite to the source I and the source II. The receiving planes of the planar array detectors are perpendicular to the plane where a transmission platform of the conveyance means of the mechanical conveyance unit 102 is located. The receiving planes of the two sets of planar array detectors form an angle of 90 degrees.

The imaging unit 104 is a computer work station for performing work such as control, data transmission, image reconstruction and data processing of the entire security inspection system.

After the transmission projection body data received by the two sets of planar array detectors of the data collecting unit 103 are inputted into the computer work station, the computer work station reconstructs the projection data received by the straight-line filtered backprojection algorithm as a perspective image, a tomographic image or a 3-D image of the inspected image and displays the reconstructed perspective image, tomographic image or 3-D image on the display.

Figure 4:
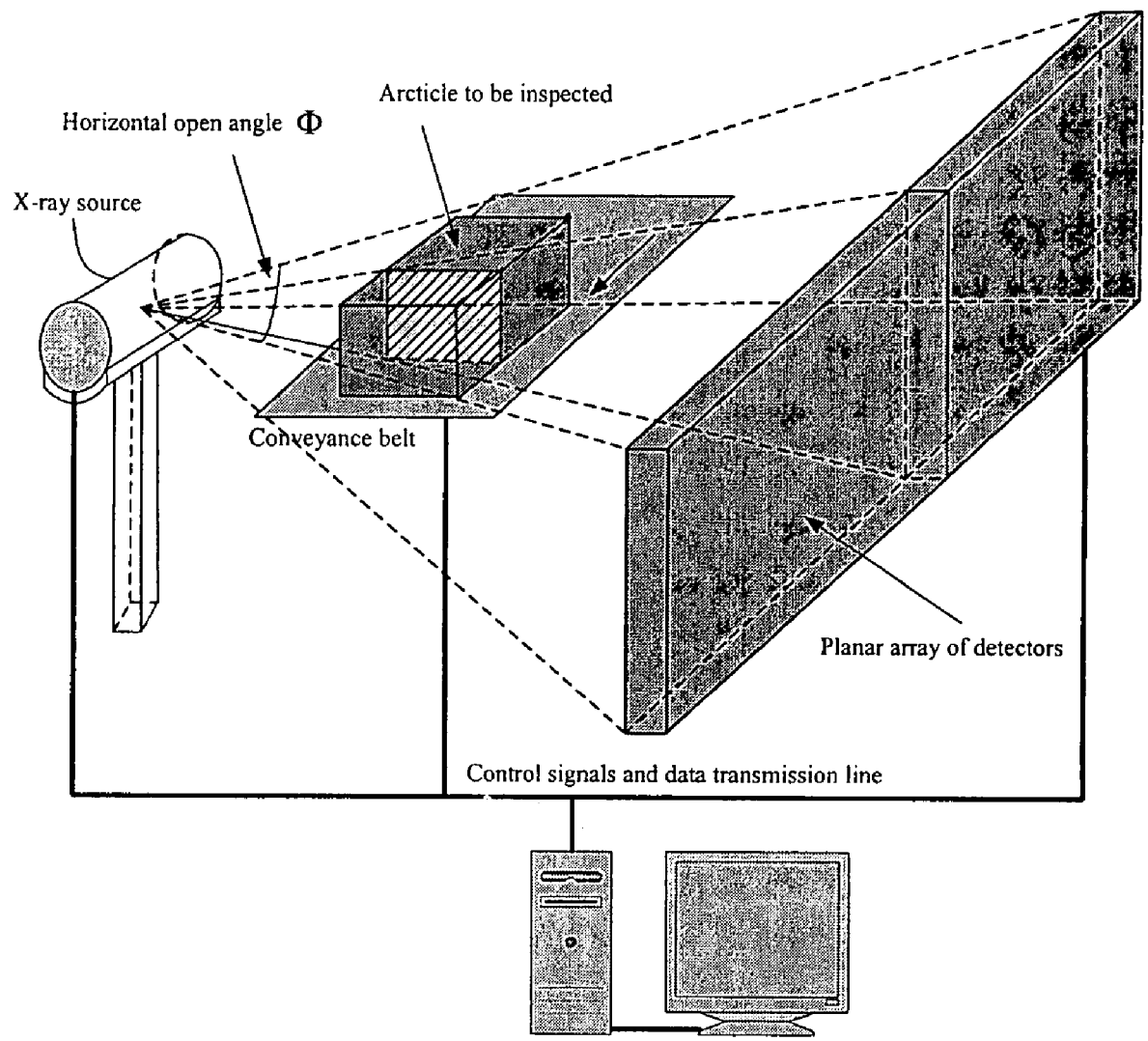
FIG. 4 is a schematic view showing scanning on a single linear sub-path in the cargo security inspection system of FIG. 3.

FIG. 4 is a schematic view showing scanning on a single linear sub-path of the cargo security inspection system of FIG. 3. The X-ray source emits ray beams with a horizontal opening angle of Φ to irradiate, in the horizontal direction, the inspected object that moves on the conveyance belt at a uniform speed; the ray beams, after transmitting through the inspected object, reaches the receiving planes of the planar array detectors; said receiving planes of the planar array detectors receive the transmission projection data of the ray beams and combine them into projection data of the ray beams for output to a computer; and the computer carries out image reconstruction of the received projection data according to the straight-line filtered backprojection algorithm and then displays the reconstructed image on the display.

Figures 1, 5:
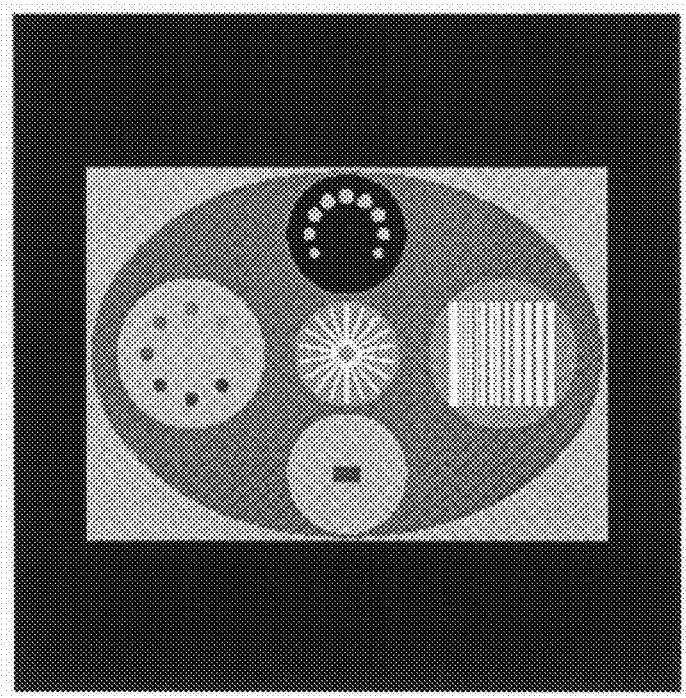
FIG. 5 is a schematic view of a tomographic image of collected data in the xy plane when a 3-dimensional image is reconstructed by using the straight-line filtered backprojection algorithm based on FIG. 3.
Figures 2, 5:
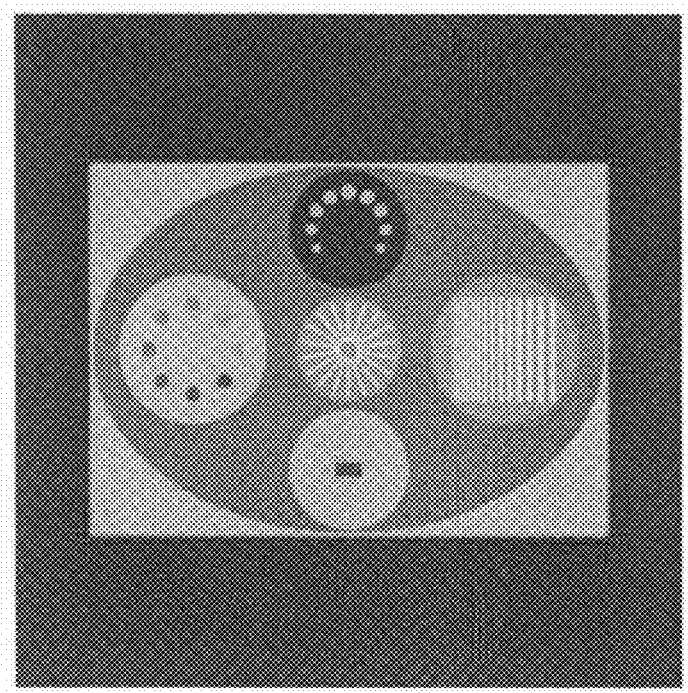
Figures 1, 6:
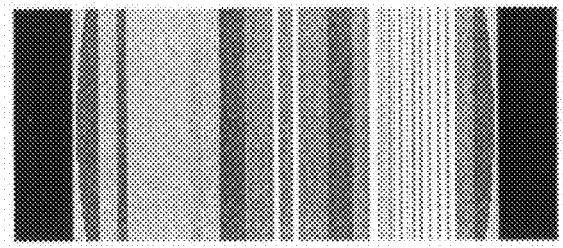
FIG. 6. shows tomographic images reconstructed by using the straight-line filtered backprojection algorithm based on FIG. 3 and the perspective image obtained by the system of the present invention.
Figures 2, 6:
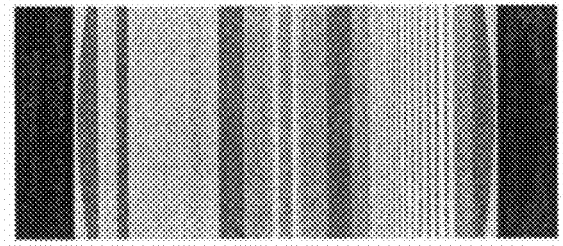
Figures 3, 6:
Figures 4, 6:
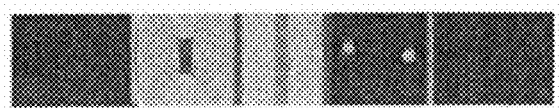
Figures 5, 6:
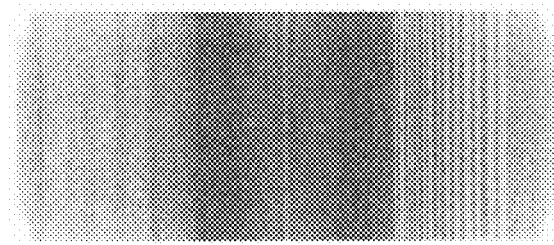

In this embodiment, when the cargo security inspection system reconstructs tomographic images by using the straight-line filtered backprojection algorithm, the tomographic image of collecting data in xy plane is shown in FIG. 5, and the reconstructed tomographic image and the perspective image acquired by the system are shown in FIG. 6.

FIG. 5 is a view regarding a simulated experiment results by using a luggage model, showing the reconstruction results at the center layer. FIG. 5-1 is an original view of the model; FIG. 5-2 is a schematic view of the reconstructed tomographic image in the xy plane.

In FIG. 6, the four views sequentially arranged in the upper portion are respectively schematic views showing the original view and the perspective image in xz plane and yz plane before and after reconstruction of the luggage model, wherein FIG. 6-1 is a schematic view of the original view in the center layer of the xz plane before the reconstruction of the luggage model, FIG. 6-2 is a schematic view of the perspective image in the center layer of the xz plane after the reconstruction of the luggage model, FIG. 6-3 is a schematic view of the original view in the center layer of the yz plane before the reconstruction of the luggage model, and FIG. 6-4 is a schematic view of the perspective image in the center layer of the yz plane after the reconstruction of the luggage model. FIG. 6-5 is a schematic view of the perspective image in the xz plane after the reconstruction of the luggage model.

Embodiment 2

FIG. 7 is a plan view of the cargo security inspection system involving imaging at multiple linear sub-paths according to the second embodiment of the present invention.

In this embodiment, the scanning of the entire security inspection system is composed of four linear sub-paths. There are four X-ray sources, i.e., source I, source II, source III and source IV serving as the radiation-generating unit. Said source I, source II, source III and source IV can be an X-ray tube, an accelerator source or an isotope source. Specific types of X-ray sources used depend on the dimensions of the inspected object and the practical application occasions.

Each of the X-ray sources emits ray beams within an opening angle of 45 degrees and the sum of angles formed between the receiving planes of detector arrays and the corresponding sources is 180 degrees.

The control means in the mechanical conveyance unit controls the conveyance means to carry the inspected object to translate along the movement sub-path I, the movement sub-path II, the movement sub-path III and the movement sub-path IV at a uniform speed, and furthermore, the inspected object does not rotate when moving at a uniform speed at the joints of the movement sub-paths.

The data collecting unit 4 is four sets of planar array detectors respectively located opposite to the source I, the source II, the source III and the source IV. The receiving planes of the planar array detectors are perpendicular to the plane where a transmission platform of the conveyance means of the mechanical conveyance unit is located. The receiving planes of two adjacent sets of planar array detectors form an angle of 130 degrees.

The imaging unit is a computer work station for performing work such as control, data transmission, image reconstruction and data processing of the entire security inspection system.

After the projection data received by the four sets of planar array detectors of the data collecting unit are inputted into a computer work station, the computer work station reconstructs the received projection data as a perspective image, a tomographic image or a 3-D image of the inspected image according to the straight-line filtered backprojection algorithm and displays the reconstructed perspective image, tomographic image or 3-D image on the display.

In this embodiment, the results of the tomographic image reconstructed by the straight-line filtered backprojection algorithm or the tomographic image and perspective image reconstructed by the straight-line filtered backprojection algorithm are the same as in the Embodiment 1 which is described above. For the sake of succinctness, depictions will not be given in detail any more herein.

The above are only embodiments of the present invention and not used to limit the present invention. According to the contents disclosed in the present invention, a person having ordinary skill in the art can apparently think of some identical, alternative solutions which should all be included in the protection scope of the present invention.

What is claimed is:

1. A cargo security inspection system for inspecting an inspected object moving through said system, the system comprising:

a mechanical conveyance unit configured to carry and convey the inspected object and to define a travel path of the inspected object in the system;

a radiation-generating unit configured to generate ray beams for transmitting through the inspected object;

a data collecting unit configured to collect transmission data about the ray beams subsequent to the transmission of the ray beams through the inspected object and process the transmission data;

wherein:

the travel path of the inspected object comprises at least two linear sub-paths that are arranged at an angle relative to each other;

the data collecting unit comprises at least two detector arrays for receiving the ray beams, each detector array corresponding to a respective one of the at least two linear sub-paths, a receiving plane of each of the detector arrays being disposed parallel to the linear sub-path to which the respective detector array corresponds; and the system is configured such that, during inspection of the inspected object, the radiation-generating unit and the data collecting unit remain stationary and to cause the inspected object to travel along the travel path with unchanged orientation, the inspected object thereby being at different respective angles relative to the at least two detector arrays and thereby being penetrable by the ray beams at different angles to reach the respective detector arrays.

2. The system according to claim 1, further comprising:
an imaging unit, wherein the data collecting unit combines the collected transmission data into projection data for outputting to the imaging unit, and the imaging unit reconstructs the projection data as an image.

3. The system according to claim 2, further comprising:
a display unit adapted for displaying the image constructed by the imaging unit.

4. The system according to claim 2, wherein the data collecting unit further comprises:
a signal conversion circuit for converting the ray beams received by the detector arrays into the transmission data;
a data processing circuit for combining the transmission data from the signal conversion circuit into the projection data; and
a logic control circuit for controlling synchronous performance of the detector array receiving the ray beams and the data processing circuit transmitting the projection data.

5. The system according to claim 4, wherein a sum of open angles of the receiving planes of the detector arrays relative to their respective radiation sources is substantially 180 degrees.

6. The system according to claim 2, wherein the imaging unit reconstructs the projection data as a tomographic image.

7. The system according to claim 6, wherein the imaging unit generates the tomographic image by a straight-line filtered backprojection algorithm.

8. The system according to claim 7, wherein the detector arrays are planar array detectors, and the imaging unit further combines a plurality of tomographic images as a 3-dimensional image.

9. The system according to claim 2, wherein the imaging unit combines the projection data to form one of (a) a perspective image at a view angle and (b) a plurality of perspective images at a plurality of view angles.

10. The system according to claim 2, wherein the imaging unit treats the projection data by adopting one of (a) any combination of and (b) one of a group of five processing manners including: inconsistency of detectors, hardening, scatter correction, metal artifacts correction, and image processing and pattern recognition.

11. The system according to claim 10, wherein the image processing and pattern recognition comprises one of (a) any combination of and (b) one of a group of three processing modes including: image enhancement, edge detection, and hazardous article intelligent identification.

12. The system according to claim 1, wherein the radiation-generating unit comprises one of:
one radiation source which is shared by all of the detector arrays; and a plurality of radiation sources with each of the detector arrays corresponding to a respective one of the radiation sources.

13. The system according to claim 1, wherein the mechanical conveyance unit comprises:
a conveyance means for the carrying and conveying; and
a control means for controlling the movement of the inspected object along the travel path.

14. The system according to claim 1, wherein the travel path of the inspected object further comprises a joint portion between adjacent linear sub-paths of the at least two linear sub-paths.

15. The system according to claim 14, wherein the mechanical conveyance unit is configured to cause the inspected object to travel along the travel path at a uniform speed.

16. The system according to claim 1, wherein the mechanical conveyance unit is configured to cause the inspected object to travel along the travel path at a uniform speed.

17. The system according to claim 1, wherein the radiation-generating unit and the data collecting unit are provided on different sides of the travel path.

18. The system according to claim 1, wherein the detector arrays are one of linear array detectors and planar array detectors.

19. The system according to claim 18, wherein the linear array detectors are arranged at one of an equal distance from each other and an equal angle with respect to each other, and the planar array detectors are one of flat-panel detectors, cylindrical detectors, and L-shaped detectors.

20. The system according to claim 1, wherein the travel path of the inspected object is in a horizontal plane and the ray beams have horizontal opening angles.

21. A cargo security inspection method for inspecting an inspected object moving through an inspection system, the method comprising:
carrying the inspected object;
conveying the inspected object so that the inspected object travels with an unchanged orientation along at least two linear sub-paths of a defined travel path in the system, the at least two linear sub-paths being arranged at an angle relative to each other;
generating ray beams by a radiation-generating unit;
transmitting the ray beams through the inspected object;
receiving the ray beams by a data collecting unit comprising at least two detector arrays, each detector array corresponding to a respective one of the at least two linear sub-paths, a receiving plane of each of the detector arrays being disposed parallel to the linear sub-paths to which the respective detector array corresponds;
the data collecting unit collecting transmission data about the ray beams subsequent to the transmission of the ray beams through the inspected object;
the data collecting unit processing the transmission data; and
maintaining the radiation-generating unit and the data collecting unit in a stationary position throughout the inspection, the inspected object thereby being at different respective angles relative to the at least two detector arrays and thereby being penetrable by the ray beams at different angles to reach the respective detector arrays.

22. The method according to claim 21, wherein the travel path of the inspected object is in a horizontal plane and the ray beams have horizontal opening angles.

* * * * *